United States Patent [19]

Ito

[11] Patent Number: 4,615,805
[45] Date of Patent: Oct. 7, 1986

[54] METHOD FOR CONTINUOUS COUNTERCURRENT FOAM SEPARATION

[75] Inventor: Yoichiro Ito, Bethesda, Md.

[73] Assignee: The United States of America as represented by the Department of Health and Human Services, Washington, D.C.

[21] Appl. No.: 776,044

[22] Filed: Sep. 13, 1985

[51] Int. Cl.⁴ ............................................. B01D 15/08
[52] U.S. Cl. ................................. 210/657; 210/198.2
[58] Field of Search ................... 210/511, 657, 198.2, 210/635

[56] References Cited

U.S. PATENT DOCUMENTS 4,058,460 11/1977 Ito ........................................ 210/657
4,287,061 9/1981 Sutherland ........................ 210/198.2

Primary Examiner—Frank Sever
Attorney, Agent, or Firm—Browdy and Neimark

[57] ABSTRACT

A method of performing foam separation utilizes a gas-liquid dual countercurrent flow through a helical column subjected to a particular type of synchronous planetary motion. Samples introduced at the middle portion of the column, either continuously or batch wise, are separated according to the foam affinity. Any material having an affinity to the foam is quickly carried with the foaming stream and eluted through one end of the column, whereas other materials are carried with the liquid stream in the opposite direction and eluted out through the other end of the column.

4 Claims, 10 Drawing Figures

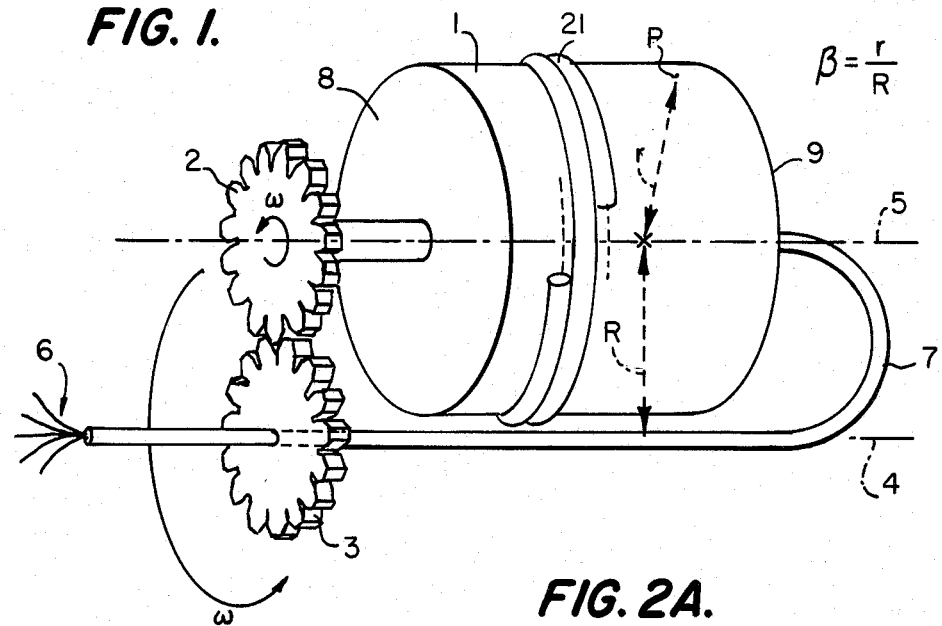
$\beta = \frac{r}{R}$
FIG. 2A.
UNILATERAL HYDRODYNAMIC EQUILIBRIUM IN A CLOSED COIL
FIG. 2B.
ONE-WAY ELUTION MODES
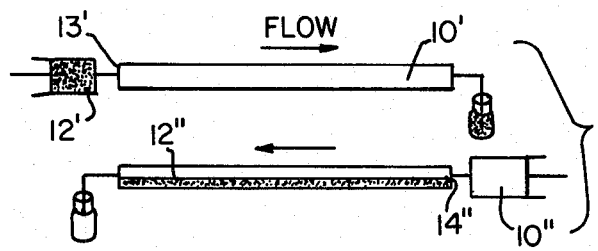
FIG. 2C
DUAL COUNTERCURRENT SYSTEM
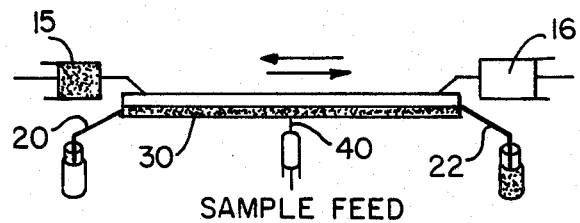
SAMPLE FEED

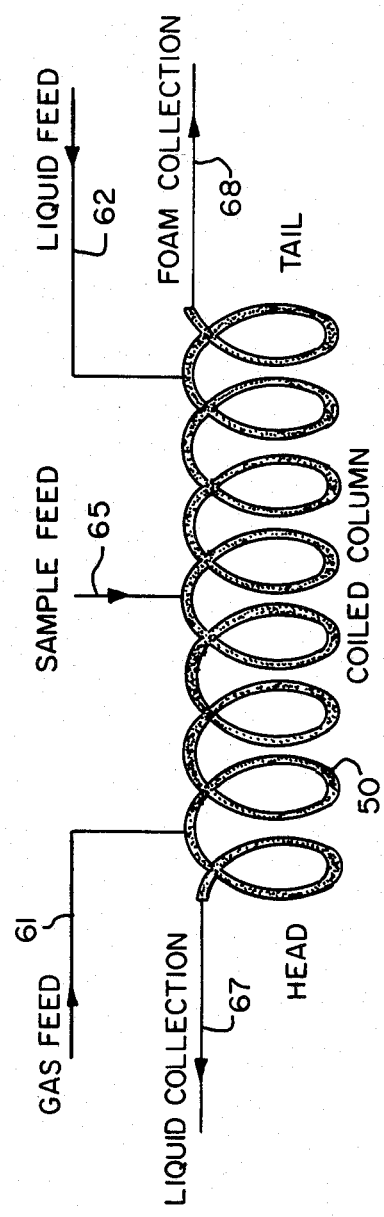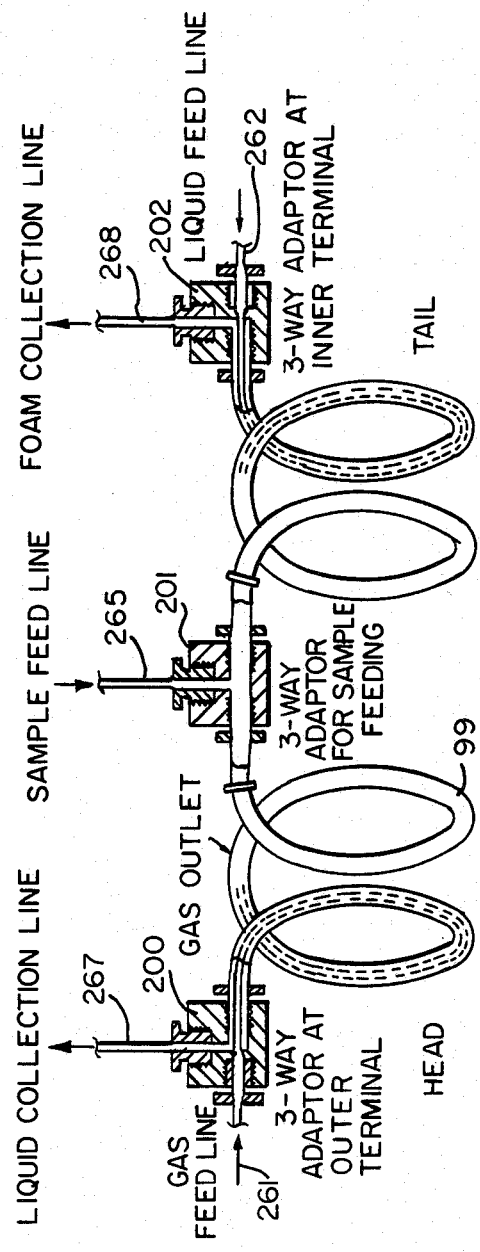

METHOD FOR CONTINUOUS COUNTERCURRENT FOAM SEPARATION

FIELD OF THE INVENTION

This invention relates to continuous countercurrent chromatography and, more particularly, to a continuous countercurrent chromatography system that separates samples based on foam affinity and which employs a dual countercurrent system.

BACKGROUND OF THE INVENTION

A variety of countercurrent chromatographic methods developed in the past (see Y. Ito, Development of Countercurrent Chromatography, Anal. Chem., 5b,534A, 1984) utilize a stationary phase that is permanently retained in the separation column through which the mobile phase is continuously eluted. This ordinary elution mode, common with many other chromatographic methods, is applied to a batch separation to yield a chromatographic separation of solutes locally charged as a discrete sample volume. Versatility of these methods, however, can be further increased if the system permits continuous separation by continuous sample feeding.

An application of countercurrent chromatography is foam separation. Although the foam separation method has been widely used during the past fifty years (see P. Somasundaran, Foam Separation Methods, Sep. Purif. Methods, 1, 117, 1972), the method has remained rather primitive and insufficient, thus largely limiting its application to use in research laboratories.

A developed countercurrent chromatographic method called high speed countercurrent chromatography (CCC), see U.S. Pat. No. 4,430,216, utilizes a particular combination of coil orientation and planetary motion to produce a unique hydrodynamic effect which permits a true countercurrent flow of the two solvent phases through the coiled column. With a proper column design the two phases can be simultaneously eluted through the column in opposite directions while the sample solution is continuously fed to the middle portion of the column. This dual countercurrent system provides a rich domain of applications such as continuous extraction, enrichment and stripping as well as continuous separation of solutes and particles.

SUMMARY OF THE INVENTION

Accordingly, an object of the invention is to provide for improved separation of materials.

Another object of the present invention is to provide a foam CCC system which overcomes the deficiencies and disadvantages of previous methods.

A further object of the invention is to provide means of foam separation of samples having a direct affinity to the gas liquid interface, e.g. detergents and other foam producing materials.

It is another object of the invention is to provide means of foam separation of samples with affinity to the foam producing carrier or collector molecule. These samples which lack a direct affinity to the gas-liquid interface can be indirectly adsorbed to the foam if they have an affinity to the foam-producing agents lining the gas-liquid interface in the foams. This type of affinity effectively used for foam separation may vary in a wide range from a non-specific form such as surface electric charges to a highly specific form such as enzyme-substrate or enzyme-inhibitor binding provided that one of the pair has either direct or indirect foam affinity.

Yet another object of the invention is to provide a foam CCC system yielding a relatively high flow rate under a unit gravitational field.

A still further object of the invention is to provide a dual CCC system for continuous extraction enrichment and stripping as well as continuous separation of solutes and particles.

A still further object of the invention is to provide a proper column construction for the dual CCC system, in which the foam CCC can be used successfully and efficiently for separation of a wide range of various materials such as dyes, enzymes, membrane receptors, proteins, etc.

To accomplish these as well as other objectives, the present invention uses a particular form of dual countercurrent system in which one of the solvent phases is replaced with a gas phase to produce foam to collect the foam active materials. In this foam CCC, the foaming stream moves from one end, the "head", toward the other end, the "tail", opposite to the liquid stream moving from the tail toward the head of the coil.

In a typical operation mode, a liquid phase containing surfactant and $N_2$ gas are simultaneously introduced through respective lines into the rotating column while the sample solution is continuously fed through the sample feed line. Consequently, the samples are separated according to their foam affinity. Solutes or particulates having an affinity to the foam are quickly carried with the foaming stream toward the tail and harvested through the foaming collection line while other materials in the sample solution are carried with the liquid stream in the opposite direction toward the head and eluted out through the liquid collection line.

BRIEF DESCRIPTION OF THE DRAWINGS

Further objects and advantages of the invention will become apparent from the following detailed description of embodiments taken in conjunction with the accompanying drawings, wherein:

FIG. 1 is a schematic perspective diagram illustrating a coil subjected to a type of synchronous planetary motion which may be employed in the present invention.

FIGS. 2A-2C are a series of schematic illustrations showing the mechanism of the dual countercurrent system, which allows simultaneous elution of the two phases through the coil in the opposite direction while the sample solution is continuously fed.

FIG. 3 is a schematic illustration of a column design according to the invention.

FIG. 5 is a schematic layout of five flow channels on a foam CCC column according to the invention.

DETAILED DESCRIPTION OF THE INVENTION

Figure 4:
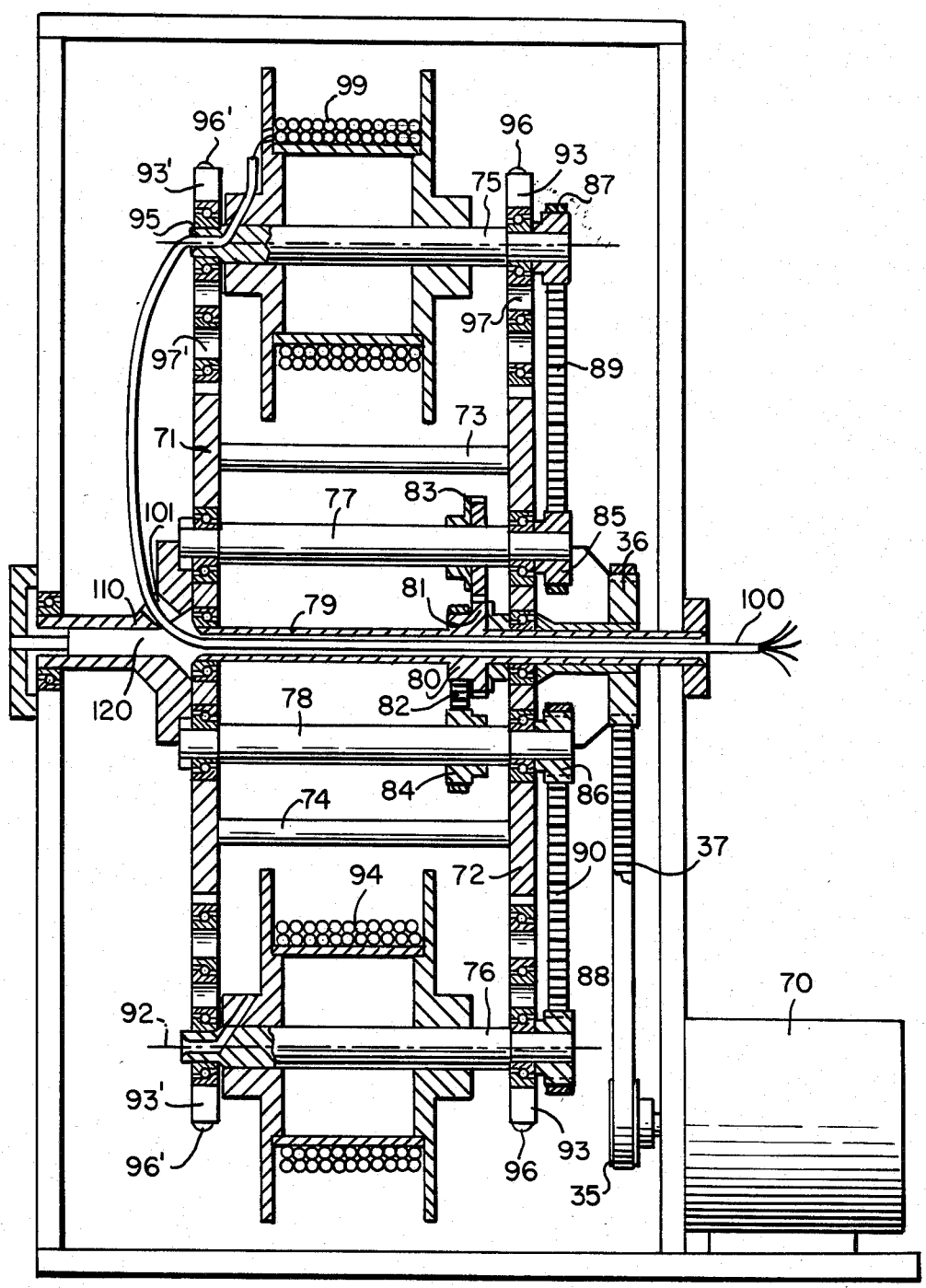
FIG. 4 is a detailed vertical cross-sectional view of a preferred embodiment of an apparatus according to the present invention.

As briefly mentioned earlier, the dual countercurrent system provides the basis for foam CCC. Therefore, first the principle of the dual countercurrent system is described below.

Dual Countercurrent System

Referring to FIG. 1, a cylindrical coil holder 1 is equipped with a planetary gear 2 which is coupled with an identical stationary sun gear 3 placed around the central axis 4 of the centrifuge. This gear arrangement produces a particular type of synchronous planetary motion of the holder 1. The holder 1 rotates about its own axis 5 and simultaneously revolves around the central axis 4 of the centrifuge at the same angular velocity ω in the same direction. This synchronous rotation of the holder unwinds the twist of the flow tubes 6 caused by revolution, thus eliminating the need for the rotary seals. Consequently, the system permits the use of multiple flow channels for performing continuous elution through the rotating column without complications such as leakage and contamination often caused by the rotary seals. This unique capability of the flow-through centrifuge system enables the successful operation of the dual countercurrent elution which necessitates the use of five flow-through channels 6, some under considerably high pressures which may be 80 psi or more.

The channels 6 meet to form the tubing 7 as will be described in more detail below.

When such tubing is coaxially wound around the holder 1, the above synchronous planetary motion of the holder 1 distributes the two solvent phases in the coiled portion 21 of the tube in such a way that one phase entirely occupies the head side 8, and the other phase the tail side 9 of the coil. Here, the head-tail relationship of the coil is determined by the Archimedean screw force acting on the coil contents: all objects tend to move from the tail toward the head of the coil. The above unilateral phase distribution renders a unique application to the dual countercurrent system described next. The parameter β determines the pattern of the centrifugal force field produced by the planetary motion as is known (Y. Ito, J. Chromatogr., 301, 377, 1984).

The mechanism of the dual countercurrent system is illustrated in FIG. 1 where all coiled tubes are schematically drawn uncoiled to indicate the relative volume distribution of the two solvent phases along the length of the tube. In FIG. 2A the unilateral hydrodynamic equilibrium distributes the white phase 10 in the head 13 half and the black phase 12 in the tail 14 half. This hydrodynamic equilibrium condition clearly indicates that the white phase 10, if introduced into the black phase 12, would move toward the head 13; and the black phase 12, if introduced into the white phase 10, would move toward the tail 14. Consequently, the system can be efficiently applied for performing CCC in two different ways.

Thus, noting FIG. 2B, the coil can be first entirely filled with the white phase 10' and the black phase 12' is then pumped through the head 13' of the coil (FIG. 2B, top). Alternatively, the coil can be first entirely filled with the black phase 12" and the white phase 10" is pumped through the tail 14" of the coil (FIG. 2B, bottom).

The system further permits, noting FIG. 2C, simultaneous introduction of the two phases 15, 16 through the respective ends of the coil to produce true countercurrent flow. This requires an additional flow channel 20, 22 at each end of the coil 30 to collect the effluent and also a sample feed line 40 at the middle portion of the coil 30. This dual countercurrent system can be applied to the foam separation as described below.

Foam CCC

As previously explained the dual CCC described above should be modified for foam CCC.

FIG. 3 illustrates a schematic column design for foam CCC. The coiled column 50 is equipped with five flow channels 61, 62, 65, 67 and 68. The liquid phase is introduced through the liquid feed line 62 located near the tail and drained through the liquid collection line 67 at the head of the coil. The gas phase is similarly introduced through the gas feed line 61 located near the head and the generated foams are harvested through the foam collection line 68 at the tail of the coil. The sample solution may be introduced through the sample feed line 65 opened at the middle portion of the coil.

FIG. 4 shows a cross-sectional view through the central axis of a preferred apparatus. A motor 70 drives a rotary frame consisting of a pair of aluminum plates 71 and 72 rigidly bridged with links 73 and 74, and which holds symmetrical column holders 75 and 76, and countershafts 77 and 78, by means of toothed pulleys 35, 36 and the toothed belt 37. Each column holder 75, 76 is subjected to a different type of synchronous planetary motion. Among these, the gear-driven holder 75, which produces the suitable planetary motion, is exclusively employed for the present invention.

The rotary frame embeds a central stationary pipe 79, which is equipped with a stationary gear 81 and a stationary toothed pulley 80 for providing the desired planetary motion to each holder 75, 76.

The stationary gear 81 is coupled to an identical gear 83 on the countershaft 77 to produce rotation of the centershaft 77 on the rotary frame. This motion is further conveyed to the holder 75 with a pair of toothed pulleys 85, 87 and a toothed belt 89. This arrangement produces a desired planetary motion of the holder 75, i.e. rotation about its own axis 91 and revolution around the central axis of the centrifuge at the same angular velocity.

The central stationary pulley 80 is coupled with a toothed belt 82 to an identical pulley 84 on the countershaft 78 to produce counterrotation of the countershaft 78 on the rotary frame. This motion is similarly conveyed to the holder 76 with a pair of toothed pulleys 86, 88 and a toothed belt 90. Consequently, the pulley-driven holder 76 counterrotates about its own axis 92 as it revolves around the central axis of the centrifuge. This type of planetary motion, though applicable to the foam separation method (see Y. Ito and R. L. Bowman, Separation Science, 11 (3), 201, 1976), tends to produce high column pressure and constant discharge of the gas phase through the liquid collection line. In a more preferred embodiment the holder 76 is used to mount a counterweight 94 for balancing the centrifuge.

Each holder 75, 76 is made removable from the rotary frame by loosening a pair of screws 96, 96' on each bearing block 93, 93'. The position of the holder 75, 76 on the rotary frame is adjustable to 15 cm or 20 cm from the central axis of the centrifuge by choosing the respective bearing holes 95, 97, 97'.

The separation column 99 is prepared from a 10 m long, 2.6 mm i.d. PTFE tube (Zeus Industrial Products, Raritan, N.J.) by winding it coaxially onto the holder 75 (12.5 cm diameter) making two coiled layers with a total capacity of about 50 ml. In order to facilitate the countercurrent process, the head terminal is located at the outer layer and the tail terminal at the inner layer of the coiled column 99.

Overall layout of the flow lines on the coiled column 99 is illustrated in FIG. 5. Each terminal is equipped with a 3-way Kel-F (polytrifluoromonochloroethylene) adaptor 200, 202 which connects inlet flows tubes 261, 262 and outlet flow tubes 267, 268 to the coiled column 99 whereas at the middle portion of the column a sample feed tube 265 opens through a 3-way Kel-F adaptor 201. At each terminal the feed line 261, 262 is passed through the adaptor 200, 202 to extend into the separation column 99 for about 50 cm or one complete helical turn. This prevents the introduced phases from flowing back toward the immediate outlet opening at each terminal. The foam collection line 268 and liquid collection line 267 are desirably made of 0.85 mm i.d. PTFE tubes and other three feed lines 261, 262, 265 of 0.55 mm i.d. tubes. In the actual configuration of the coiled column (e.g. FIG. 5), consisting of the double layers, the first and second coil layers have different handedness.

Referring again to FIG. 4, the five flow tubes from the separation column 99 as described above are bundled, lubricated with silicone grease and protected with a piece of flexible tubing (Tygon) to prevent direct contact with metal parts. The tube bundle 100 is first led through the hole 95 of the holder shaft and then passed through the side hole 101 of coupling pipe 110 mounted on the central axis to reach the opening 120 of the central stationary pipe 79. These flow tubes are free from twisting and can last several months to one year under the normal operational conditions.

The rotational speed of the apparatus is continuously adjustable up to 1000 rpm. In an initial study, however, the rate was limited to 500 rpm (about $56 \times g$ on the holder axis). The preliminary experiments for foam CCC were performed with a table top model of the combined horizontal flow-through coil planet centrifuge at a 20 cm revolutional radius (see Y. Ito, J. Chromatogr., 301, 377, 1984).

Two metering pumps (Milton Roy Minipump) were used to pump the liquid phase, one through the liquid feed line and the other through the sample feed line, whereas $N_2$ gas was introduced through the gas feed line at constant pressure of 80 psi which produced a gas flow rate of 600 ml/min measured at the outlet of the foam collection line. The flow rate through the liquid collection line was regulated by the use of a needle valve (Model SS-1SG, Potomac Valve & Fitting, Inc., Rockville, MD) equipped with a 50 cm length of 0.3 mm i.d. PTFE tubing at the outlet of the valve to restrict the flow rate. The foam collection line was left open without restriction, the foam collection rate being determined by the difference between the sum of the liquid feed rates (through the liquid feed line and sample feed line) and the liquid collection rate through the liquid collection line.

Reagents

Rhodamine B and Evans blue were obtained from Fisher Scientific Company, Pittsburgh, PA; sodium dodecyl sulfate (SDS) and 35% bovine serum albumin (BSA) from Sigma Chemical Company, St. Louis, MO; and sodium phosphates from J. T. Baker Chemical Company, Phillipsburg, N.J. Methanol used for absorbance measurement was obtained from Burdick and Jackson Laboratories, Inc., Muskegon, MI.

Preparation of Hemoglobin Solution

About 3 ml of EDTA-treated sheep blood was delivered into a 12 ml graduated plastic centrifuge tube and spun at 2000 rpm for 10 min. Then, the supernatant plasma was removed and the red cell sediment was washed with 10 ml of 0.9% saline solution three times by repeating gentle mixing, centrifugation and decanting the supernatant. Finally, 1 ml of loosely packed red cells was mixed with 9 ml of distilled water for hemolysis. The protein sample mixture was prepared by combining equal volumes of the above hemoglobin solution and 0.2% BSA.

Experimental Procedures

Preliminary studies were performed in the following three elution modes.

(1) Continuous enrichment and stripping without using the sample feed lines.

A large volume of the sample solution containing a small amount of material is pumped through the liquid feed line at constant pressure of 80 psi. The enriched foam is continuously collected through the foam collection line and the stripped liquid through the liquid collection line.

(2) Batch separation with sample injection through the sample feed line.

Continuous countercurrent streams of gas and liquid phases are introduced along the length of the column by pumping the liquid phase through the liquid feed line under $N_2$ gas pressure of 80 psi applied through the gas feed line. After the steady state hydrodynamic equilibrium is established, a small volume of the sample solution is locally injected through the sample feed line. Foam and liquid eluted through the respective collection lines are separately fractionated into a series of test tubes at suitable intervals.

(3) Continuous separation by continuous sample feeding through the sample feed line.

The steady state equilibrium of the gas liquid countercurrent flow is first established in the column as in the batch separation experiment described above. Then, the sample solution is continuously introduced through the sample feed line. Foam from the foam collection line and the effluent from the liquid collection line are each separately collected into a graduated cylinder.

Sample Analysis

Analysis of dye fractions was made by diluting an aliquot of each fraction with methanol and measuring the absorbance with a Zeiss spectrophotometer. Rhodamine B and Evans blue were analyzed at 556 nm and 620 nm, respectively. The absorbance values were multiplied with the dilution factor and the total fraction volume to determine the relative sample dose in each fraction. A minute amount of rhodamine B present in the stripped sample solution was fluorometrically analyzed with an Aminoco Bowman Fluorometer using the excitation and emission wavelengths at 560 nm and 600 nm, respectively. Analysis of protein fractions was performed by diluting each fraction with distilled water and measuring the absorbance at 280 nm and 540 nm for BSA and sheep hemoglobin, respectively.

RESULTS

The initial studies were performed to demonstrate the capability of the foam CCC method under a set of experimental conditions listed above. Because of a large number of factors involved, no attempt was made to optimize all those conditions. Instead, efforts were directed to select one workable set of experimental conditions for exploration of the potential capability of the method.

Continuous enrichment and Stripping

This study was performed to demonstrate the capability of the method to concentrate and/or eliminate a minute amount of material present in a large volume of sample solution. The sample solution containing rhodamine B at a $10^{-6}$ M concentration and SDS at $10^{-3}$ M as a collector was introduced, through the liquid feed line at 214 ml/h against $N_2$ flow through the gas feed line at 80 psi, while the apparatus was run at 500 rpm. The sample feed line was not used in this experiment. The liquid collection rate was adjusted at a level slightly below the liquid feed rate so that the foam collection rate became as small as several hundred microliters per hour which yielded the foam highly enriched with rhodamine B. After 1 liter of the sample solution wa eluted, the liquid collection line was closed to elute rhodamine B remaining in the column through the foam collection line. The stripped liquid collected through the liquid collection line was fluorometrically analyzed to determine the concentration of rhodamine B. The results showed that the dye concentration in the stripped solution was $1.3 \times 10^{-9}$ M while over 99% of rhodamine B was recovered through the foam collection line within a 2 ml volume resulting in over 500-fold enrichment.

Batch Separation with Sample Injection through Sample Feed Line

This study was initiated by establishing a liquid-gas countercurrent flow equilibrium through the coiled column. At the revolutional speed of 500 rpm, surfactant solution containing SDS at $10^{-3}$ M was pumped through the liquid feed line while the $N_2$ gas flow was introduced through the gas feed line at 80 psi. After the hydrodynamic equilibrium was reached, 0.5 ml of sample solution containing rhodamine B and Evans blue each at $5 \times 10^{-4}$ M was injected through the sample feed line. The needle valve on the liquid collection line was adjusted to make a 1:3 volume ratio between the foam and liquid fractions. Effluents from both collection lines were separately fractionated into a series of test tubes at 30 second intervals. The concentration of each dye in the fractions was spectrophotometrically determined using 556 nm for rhodamine B and 620 nm for Evans blue.

Figure 6:
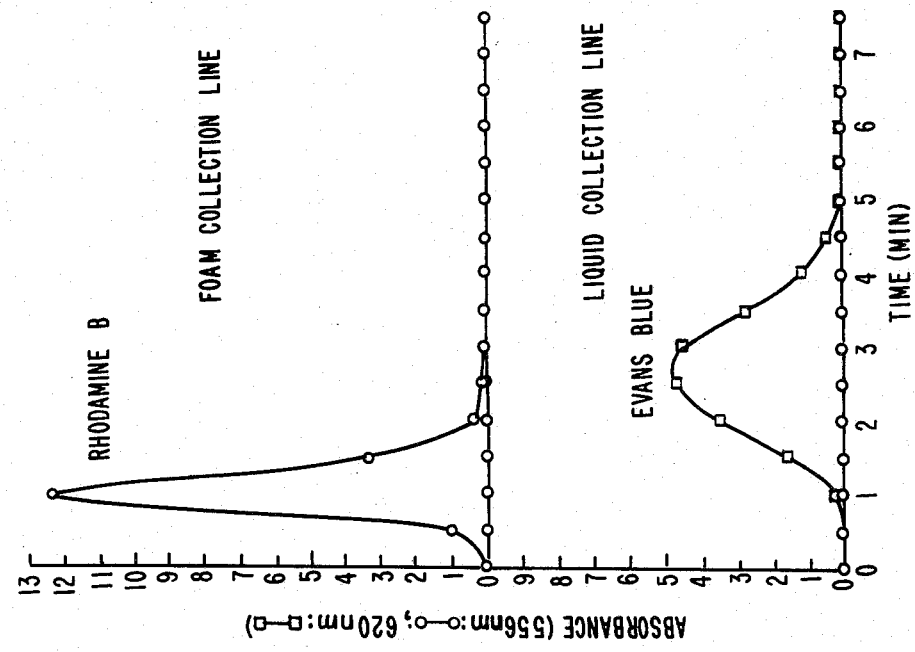

FIG. 6 shows the typical experimental result obtained with the present batch separation method. Rhodamine B having foam affinity was quickly eluted through the foam collection line (upper chromatogram) while Evans blue was carried with the liquid stream in the opposite direction and eluted through the liquid collection line (lower chromatogram). Note: In analysis, Evans blue absorbed the light at both wavelengths at a ratio of 0.6 (556 nm/620 nm). Therefore, the 556 nm curve in the lower chromatogram, which represents the elution profile of rhodamine B, was given by the total absorbance at 556 nm less the absorbance at 620 nm multiplied by 0.6. The upper chromatogram obtained through the foam collection line shows a sharp single peak entirely consisting of rhodamine B with the peak maximum at one minute after sample injection. The lower chromatogram obtained through the liquid collection line shows a broad symmetrical peak of Evans blue with the peak maximum at 2.75 minutes after sample injection. These results are quite reproducible and injection of the single component produced the similar peak through the respected collection line. The volume of the liquid phase present in the column under a steady state hydrodynamic equilibrium in these experiments ranged between 4 and 5 ml which amounted to approximately 10% of the total column capacity.

Continuous Separation by Continuous Sample Feeding through the Sample Feed Line

Rapid and clean separation of the two dyes in the batch separation method described above indicated the feasibility of continuous separation by steadily feeding the sample mixture at a proper rate. Under otherwise identical experimental conditions used in the batch separation, the sample solution was continuously introduced through the sample feed line at various flow rates. The satisfactory separations were obtained at sample feed rates of 0.36 ml/min or less, which separated each sample at the maximum rate of $1.8 \times 10^{-7}$ mol/min. The application of higher flow rates resulted in initial accumulation of rhodamine B in the column which was later followed by elution of rhodamine B through the liquid collection line.

Figure 7:
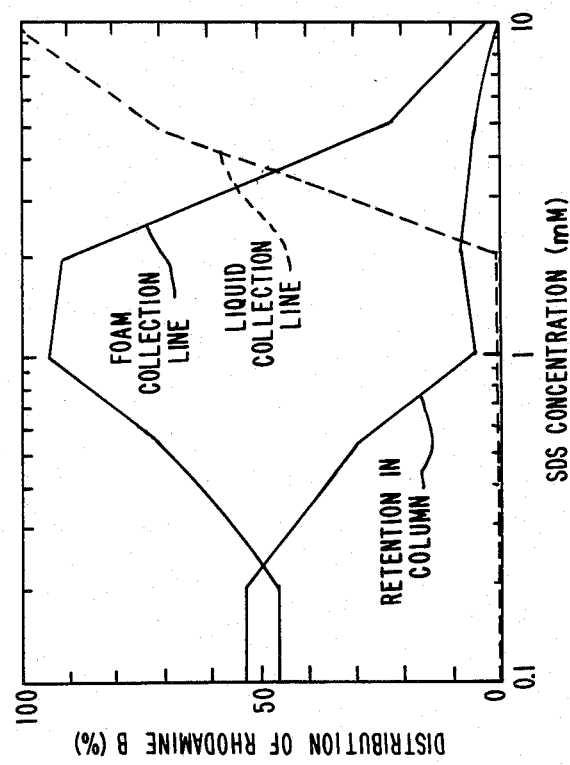
FIGS. 6-8 are graphs showing results of the present invention.

The experiments were continued to study the effects of SDS concentration on the hydrodynamic behavior of rhodamine B in the foam separation column under a high sample feed rate of $3.8 \times 10^{-7}$ mol/min. The results are summarized in FIG. 7 which shows the distribution of rhodamine B at various SDS concentrations in the liquid phase, and where the percentage distribution of the rhodamine sample is plotted for the applied SDS concentration expressed in a log scale in abscissa.

Among three curves drawn in the diagram, the thick solid curve indicates the amounts of dye eluted through the foam collection line; the thin solid curve, the amounts of dye retained within the column; and the broken curve, the amounts of dye eluted through the liquid collection line. At a high SDS concentration of $10^{31}$ $^2$ M, the dye exhibited little affinity to the foam and mostly eluted through the liquid collection line. As the SDS concentration was decreased, the dye rapidly developed the foam affinity and, at $10^{-3}$ to $2 \times 10^{-3}$ M SDS concentrations, over 90% of the dye was collected through the foam collection line while the liquid collection line eluted clear liquid almost free of rhodamine B. Further decrease of the SDS concentration resulted in a decreased foam recovery rate of rhodamine B causing the retention within the separation column.

If the sample feeding is stopped at this stage, elution of the dye through the foam collection line continues at the same rate until the retained dye is completely recovered. If the sample feeding is continued, the dye continuously accumulates in the column and finally appears through the liquid collection line. The results clearly indicate that the foam recovery rate of rhodamine B is largely governed by the SDS concentration which yields the highest recovery rate at $10^{31}$ $^3$ M to $2 \times 10^{-3}$ M under the present experimental condition.

Preliminary Study for Protein Separation

The present method was applied to the separation of proteins without the use of a surfactant collector. As is well known, exposure of proteins such as BSA to a gas-liquid interface may cause denaturation to alter the physiological function of the molecule. The preliminary studies were conducted to test vulnerability and foam-producing capacity of proteins with the present system by injecting the sample solution into the running column through the sample feed line. Several kinds of proteins including BSA, human and sheep hemoglobin, and ovalbumin were examined. Among these only BSA showed an active foam-producing ability and was collected through the foam collection line whereas other proteins were mostly eluted through the liquid collection line without any visible evidence of denaturation.

BSA fractions eluted through the foam collection line showed various degrees of turbidity apparently due to denaturation of the molecule. Further experiments revealed that the intensity of turbidity highly depended upon the composition of the applied liquid phase. The use of salt-free distilled water or dilute acid solution caused most intensive turbidity. Addition of a surfactant to the liquid phase decreased the degree of turbidity, but at the same time lowered the foam recovery rate of BSA. Sodium phosphate solution of slightly alkaline pH (7.2–8.9) at a relatively high ionic strength (0.2–0.5 M) produced minimum turbidity with a high BSA recovery of over 90% through the foam collection line.

Figure 8:
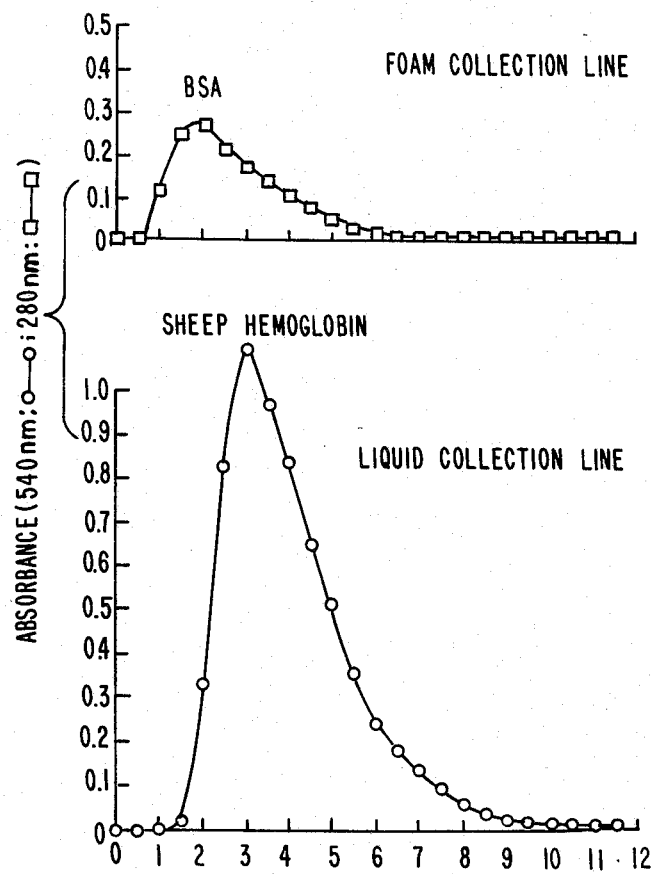

FIG. 8 illustrates results of the preliminary study of the batch separation of BSA and sheep hemoglobin obtained with a liquid phase composed of 0.2 M dibasic sodium phosphate solution (pH 8.9) under the standard experimental condition previously applied to the dye separation, using the present foam CCC method BSA having a foam-producing capacity was quickly eluted through the foam collection line and collected within 6 minutes while sheep hemoglobin was entirely recovered through the liquid collection line in about 10 minutes.

The preliminary studies on foam separation of proteins described above furnish a useful guidance for further development and practice of the present method. Although simple adjustment of pH and ionic concentration of the liquid phase worked out well for separation of BSA, many other proteins lack an active foam-producing capability and therefore require the use of selective collectors to acquire the foam affinity. The use of such collectors should also prevent the protein molecules from direct contact with the gas-liquid interface, thus reducing the possibility of denaturation.

One useful application of the present method is the separation of macromolecules or particulates with foam affinity CCC using highly specific collector molecules. For example, a long hydrocarbon chain is attached to a substrate or inhibitor molecule of the aimed enzyme to form a hydrophobic terminal so that the derived molecule acquires a foam affinity to carry the enzyme. The enzyme prebound to such collector molecules may be efficiently concentrated and isolated through the foam collection line in a short period of time. This achievement greatly contributes to a broad field of biological sciences including protein chemistry, cell physiology, and genetic engineering.

It is to be understood that the present invention is not limited to the examples disclosed above which are illustratively offered and that modifications may be made without departing from the invention.

While a specific embodiment of a foam CCC apparatus has been disclosed in the foregoing description, it will be understood that various modifications within the scope of the invention may occur to these skilled in the art. Therefore, it is intended that adaptations and modifications should and are intended to be comprehended within the meaning and range of equivalents of the disclosed embodiments.

What is claimed is:

1. A method of fast foam separation from a sample with foam affinity using centrifuge principles comprising the steps of:
   continuously extraction enriching, stripping and separating solute and particles of samples with affinity to foam producing carrier or collector molecule, in a dual CCC system,
   providing a dual countercurrent flow system including a multi-layer coiled column wrapped about a cylindrical column holder, said column holder being mounted on a rotary frame for rotation about its central longitudinal axis;
   introducing a non-reactive gaseous fluid at one end of said coiled column, said coiled column having two ends and a middle;
   introducing a liquid at the other end of said coiled column;
   rotating said column holder about said central longitudinal axis while simultaneously rotating said coiled column about a second longitudinal axis parallel to said central longitudinal axis to form a foam phase moving toward one end of said coiled column and a liquid phase moving toward the other end of said coiled column;
   introducing a sample liquid into said coiled column after equilibrium is reached between foam phase and liquid phase in said coiled column, said equilibrium being the state where generated foam existing in said coiled column is separated from liquid of said coiled column;
   rotating said coiled column having said sample therein about said central longitudinal axis while simultaneously rotating said coiled column about said second longitudinal axis to create foam phase and liquid phase from said sample;
   collecting said elements in at least one of said coiled column said coiled column ends.

2. The method of claim 1, wherein said sample can be introduced into said coiled column from said middle of said coiled column.

3. The method of claim 1, wherein said sample can be introduced into said coiled column from said end in which said liquid is introduced into said coiled column.

4. A method of performing foam separation utilizing a gas-liquid dual countercurrent flow through a helical column, comprising:
   continuously extraction enriching, stripping and separating solute and particles of samples with affinity to foam producing carrier or collector molecule, in a dual CCC system, by
   introducing a sample at the middle portion of the column;
   introducing gas at one end of the column and liquid at the other end of the column in the direction opposite to the direction of gas flow;
   rotating and revolving the column using a planetary motion to create centrifugal force; and
   collecting foam at one end of the column and liquid at the other end of the column, the foam containing material separated from the sample having a foam affinity.

* * * * *